United States Patent [19]  
Lapporte et al.

[11] 4,340,758  
[45] Jul. 20, 1982

[54] NITRATION PROCESS FOR THE PREPARATION OF 2,6-DIALKYLANILINE

[75] Inventors: Seymour J. Lapporte, Orinda; David M. Marquis, Lafayette, both of Calif.

[73] Assignee: Chevron Research Company, San Francisco, Calif.

[21] Appl. No.: 280,399

[22] Filed: Jul. 6, 1981

[51] Int. Cl.³ ............................................. C07C 85/11
[52] U.S. Cl. ................................... 564/409; 564/305; 564/419; 564/437
[58] Field of Search ....................... 564/305, 409, 419

[56] References Cited

U.S. PATENT DOCUMENTS 3,123,644  3/1964  Olin ...................................... 564/409
3,483,266  12/1969 Hill .................................. 564/409 X

FOREIGN PATENT DOCUMENTS 49-29177  8/1974  Japan .................................. 564/409

Primary Examiner—John Doll  
Attorney, Agent, or Firm—J. A. Buchanan, Jr.; T. G. DeJonghe; C. J. Caroli

[57] ABSTRACT

A process for the preparation of 2,6-dialkylaniline which comprises the reaction of 1,3-dialkylbenzene with isobutene in the presence of a hydrogen fluoride catalyst to form 1,3-dialkyl-5-tertiary-butylbenzene, which is subsequently nitrated in the presence of a soluble mercuric salt catalyst to form 2-nitro-1,3-dialkyl-5-tertiary-butylbenzene, which is then catalytically hydrogenated to give 2,6-dialkyl-4-tertiary-butylaniline, followed by pyrolysis in the presence of a heterogeneous acidic catalyst.

17 Claims, No Drawings

NITRATION PROCESS FOR THE PREPARATION OF 2,6-DIALKYLANILINE

BACKGROUND OF THE INVENTION

This invention is concerned with an improved process for the preparation of 2,6-dialkylaniline which comprises the reaction of 1,3-dialkylbenzene with isobutene in the presence of a hydrogen fluoride catalyst to form 1,3-dialkyl-5-tertiary-butylbenzene, which is subsequently reacted with nitric acid in the presence of a soluble mercuric salt catalyst to form 2-nitro-1,3-dialkyl-5-tertiary-butylbenzene, which is then catalytically hydrogenated to give 2,6-dialkyl-4-tertiary-butylaniline, followed by pyrolysis in the presence of a heterogeneous acidic catalyst.

One method of preparing 2,6-dialkylaniline is by the amination of hydroxy aromatics. U.S. Pat. No. 3,931,298 describes a process for the preparation of aromatic amines by the reaction of hydroxy-substituted aromatic compounds with ammonia in the presence of a catalytic amount of a cyclohexanone and in contact with a hydrogen transfer catalyst.

U.S. Pat. No. 3,960,962 describes a related process wherein aromatic hydroxy compounds are converted to the corresponding aromatic amine by reaction with ammonia in the presence of a cyclohexanone promoter and a catalyst comprising metallic palladium bonded to a phosphinated polystyrene resin.

In U.S. Pat. No. 3,965,182 aromatic amines are made by reacting a phenol with aluminum nitride and either ammonia or a primary or secondary amine.

U.S. Pat. No. 3,801,642 is concerned with a process for replacing an aromatic hydroxyl group with an amine group by forming a metal aryloxide from the corresponding aromatic hydroxy compound and reacting the metal aryloxide with ammonia or a primary or secondary amine in the presence of a Friedel-Crafts catalyst.

U.S. Pat. No. 4,125,560 describes the direct amination of phenols with amines by the ammonolysis of phenols in a liquid phase under pressure with an aqueous ammonia solution containing a catalytic amount of an ammonium salt.

U.S. Pat. No. 3,219,704 describes the preparation of aromatic amines by the condensation of six-membered alicyclic ketones and ammonia compound with a dehydrogenation catalyst, wherein the molar portion of the ketone is at least substantially equal to the ammonia compound.

In U.S. Pat. No. 3,442,950 aminated benzenes are prepared by catalytically reacting a cyclohexanol with an aminating agent. When cyclohexanone is present in the cyclohexanol component, the reaction is initiated in the presence of one mole of hydrogen per mole of cyclohexanone.

The use of isobutene and hydrogen fluoride to alkylate dialkylbenzenes is described in U.S. Pat. No. 2,860,169 to Schlatter.

An article by L. M. Stock and T. L. Wright in the Journal of Organic Chemistry, Vol. 44, No. 20, pp. 3467–3470 (1979), describes the mercuric acetate catalyzed nitration of 1,3-dimethylbenzene. A mixture of isomeric products is obtained, the 4-nitro isomer being the major product. The 2-nitro compound is reported to be obtained in only minor amounts.

Dialkylanilines, and in particular 2,6-dialkylanilines, are useful intermediates for a variety of compounds having herbicidal and fungicidal activity.

SUMMARY OF THE INVENTION

It has now been found that 2,6-dialkylanilines, wherein each alkyl group is a straight chain of 1–4 carbon atoms, may be prepared in high yield by a process which comprises:

(a) contacting 1,3-dialkylbenzene wherein each alkyl group is a straight chain of 1–4 carbon atoms with isobutene in the presence of a hydrogen fluoride catalyst at a temperature of from about −50° C. to about 100° C. and a pressure of from about 0 psig to about 150 psig to form 1,3-dialkyl-5-tertiary-butylbenzene;

(b) contacting the 1,3-dialkyl-5-tertiary-butylbenzene with nitric acid in the presence of a soluble mercuric salt catalyst at a temperature of from about 0° C. to about 100° C. to form 2-nitro-1,3-dialkyl-5-tertiary-butylbenzene;

(c) contacting the 2-nitro-1,3-dialkyl-5-tertiary-butylbenzene with hydrogen in the presence of a hydrogenation catalyst at a temperature of from about 0° C. to about 200° C. and a pressure of from about 0 psig to about 2000 psig to form 2,6-dialkyl-4-tertiary-butylaniline;

(d) heating the 2,6-dialkyl-4-tertiary-butylaniline at a temperature of from about 50° C. to about 500° C. in the presence of a heterogeneous acidic catalyst to thereby obtain a reaction mixture comprising 2,6-dialkylaniline and isobutene; and (e) separating 2,6-dialkylaniline from the reaction mixture.

In a preferred embodiment of the present invention, the isobutene produced in step (d) above is separated from the reaction mixture and recycled back to step (a).

Preferable 2,6-dialkylanilines prepared by this method include those wherein each alkyl group independently contains 1–2 carbon atoms, such as 2-methyl-6-ethylaniline and 2,6-diethylaniline. Most preferably, the 2,6-dialkylaniline is 2,6-dimethylaniline.

1,3-dialkylbenzenes are used as starting materials. Preferable 1,3-dialkylbenzenes include those wherein each alkyl group independently is methyl or ethyl. Especially preferred is meta-xylene. The 1,3-dialkylbenzene is reacted with isobutene in the presence of a hydrogen fluoride catalyst at a temperature from about −50° C. to about 100° C., preferably from about −10° C. to about 50° C. and a pressure from about 0 psig to about 150 psig, preferably from about 0 psig to about 30 psig, to form the desired 1,3-dialkyl-5-tertiary-butylbenzene. Generally, about 1 to 10 moles, preferably 0.9 to 1.1 moles, of isobutene are employed per mole of 1,3-dialkylbenzene.

The 1,3-dialkyl-5-tertiary-butylbenzene thus formed is reacted with nitric acid in the presence of a soluble mercuric salt catalyst at a temperature from about 0° C. to about 100° C., preferably from about 50° C. to about 80° C., to give 2-nitro-1,3-dialkyl-5-tertiary-butylbenzene. The reaction may be carried out in the presence of an organic solvent which will not interfere with the course of the reaction. Suitable organic solvents include carboxylic acids, carboxylic acid anhydrides, and the like. A preferred solvent is acetic acid. Generally about 1 to 10, and preferably about 1 to 1.2, moles of nitric acid are employed per mole of 1,3-dialkyl-5-tertiary-butyl-benzene. Nitric acid strengths employed are those well known in the art to give reasonable reaction rates and selectivities for mono-nitro compounds.

The mercuric salt should be one which is soluble in the reaction medium. Suitable soluble mercuric salts include mercuric carboxylates, mercuric nitrate, mercuric chlorate and mercuric sulfate. A preferred mercuric salt is mercuric acetate.

The 2-nitro-1,3-dialkyl-5-tertiary-butylbenzene so formed is subjected to catalytic hydrogenation to give 2,6-dialkyl-4-tertiary-butylaniline. The usual hydrogenation catalysts may be used in the hydrogenation step, among which are catalysts containing one or more elements of Group VIII of the Periodic Table as metal or oxide. Examples of suitable catalysts include platinum, palladium, nickel, cobalt, rhodium, ruthenium, iridium, osmium and mixtures thereof. Copper, molybdenum and chromium may also be utilized as the catalyst. For the purposes of the present invention, the preferred catalyst is Raney nickel or palladium.

The active component of the catalyst may be used alone or in combination with a support. Examples of suitable supports include carbon, alumina, silica, kieselguhr, aluminum silicates and the like.

Although the hydrogenation step of the present invention may be carried out in mixed liquid-vapor phase, generally it is preferred to carry out the reaction in the liquid phase. Typically, the hydrogen remains in gaseous phase except for dissolved hydrogen. Only small excesses of hydrogen are necessary. Large excess amounts of hydrogen may be used to aid contacting and for cooling purposes.

Suitable pressures during hydrogenation are from about 0 to 2000 psig, preferably from about 50 to 500 psig. Suitable hydrogenation reaction temperatures are from about 0° C. to 200° C., preferably from about 80° C. to 140° C. Generally, about 3 to 50, and preferably 3 to 3.3, moles of hydrogen are used per mole of 2-nitro-1,3-dialkyl-5-tertiary-butylbenzene.

The 2,6-dialkyl-4-tertiary-butylaniline formed in the hydrogenation reaction is then pyrolyzed at a temperature of from about 50° C. to 500° C., preferably from about 250° C. to 350° C., in the presence of a heterogeneous acidic catalyst. Suitable heterogeneous acidic catalysts include acidic clays, silica, alumina and combinations thereof. A preferred acidic catalyst is silica-alumina. The reaction proceeds to provide a mixture of 2,6-dialkylaniline and isobutene. The 2,6-dialkylaniline product is separated from the reaction mixture and purified by conventional procedures. The isobutene formed can also readily be separated from the reaction mixture by conventional methods and recycled back to the initial stage of the process as regenerated starting material.

The following examples are provided to illustrate the invention in accordance with the principles of this invention but are not to be construed as limiting the invention in any way except as indicated by the appended claims.

EXAMPLE 1

1,3-Dimethyl-5-tertiary-butylbenzene is prepared as described in U.S. Pat. No. 2,860,169. According to this procedure, 448 g. (8.0 moles) of isobutene were dissolved in 961 g. (9.0 moles) of meta-xylene at 0° C. and added over a period of 4.2 hours to 150 g. (7.5 moles) of liquid hydrogen fluoride contained in a copper flask equipped with a stainless-steel stirrer, addition-tube and gas-outlet. The flask was cooled in an ice-bath. Stirring was continued for 2 hours after the end of the addition period. The contents of the flask were poured on crushed ice, neutralized with excess potassium hydroxide and the organic phase separated, washed with sodium bicarbonate solution, dried and distilled. The final product contained 17% by weight of unconverted meta-xylene, 76% of 1,3-dimethyl-5-tertiary-butylbenzene and 7% of higher boiling products.

EXAMPLE 2

To a flask were added 80 ml. of acetic acid, 32.4 g. (0.2 mole) of 1,3-dimethyl-5-tertiary-butylbenzene and 3.1 g. (0.01 mole) of mercuric acetate. The mixture was warmed to 80° C., then cooled to 50° C., and 15.2 g. (0.24 mole) of 100% nitric acid were added slowly to maintain the temperature at 50° C. for 1 hour. The product was cooled and added to water, filtered, and the water mixture was extracted three times with petroleum ether. The product was isolated after drying the petroleum ether extracts and evaporating the petroleum ether. Gas chromatographic analysis showed a 96% conversion and an 89% selectivity to 2-nitro-1,3-dimethyl-5-tertiary-butylbenzene.

EXAMPLE 3

To an autoclave were added 93.2 g. (0.45 mole) of 2-nitro-1,3-dimethyl-5-tertiary-butylbenzene, about 8 g. of Raney nickel (rinsed three times with ethanol) and 450 ml. of absolute ethanol. The reactor was flushed with nitrogen three times and with hydrogen twice and then filled with 50 psig hydrogen. The temperature was raised to 50° C. Initially the reaction was fast and during this time the hydrogen pressure was maintained. Gradually, as the rate decreased, the hydrogen pressure was increased to 200 psig. The total reaction time was 2 hours. The combined crude products from four such runs were filtered and distilled to give 243 g. of 91% pure product, 2,6-dimethyl-4-tertiary-butylaniline, in 75% yield.

EXAMPLE 4

To a 1 liter stirred autoclave were charged 62 g. (0.3 mole) of 2-nitro-1,3-dimethyl-5-tertiary-butyl-benzene, 300 ml. of ethanol and 1.0 g. of 5% palladium on charcoal. The autoclave was purged with hydrogen and then pressure to 1000 psig at 90° C. to 95° C. After 1 hour, the reaction was stopped. A total of 500 psig were taken up. The reaction mixture was filtered through Celite and the ethanol was evaporated. The final product was distilled at 93° C. to 98° C./7 to 10 torr to yield 47.2 g. of a very pale yellow liquid. An 89% isolated yield of 99+% pure 2,6-dimethyl-4-tertiary-butylaniline was obtained.

EXAMPLE 5

7.39 g. 2,6-Dimethyl-4-tertiary-butylaniline were passed over a commercial silica-alumina cracking catalyst (Durabeads) at a temperature of 600° F. (315.5° C.) and a flow rate of 100 ml./min. of nitrogen and a flow rate of 7.5 ml./hr. of the 2,6-dimethyl-4-tertiary-butylaniline. 4.89 g. of 89% pure 2,6-dimethylaniline were obtained at 93% conversion.

We claim:

1. A process for the preparation of 2,6-dialkylaniline wherein each alkyl group is a straight chain of 1-4 carbon atoms which comprises:
   (a) contacting 1,3-dialkylbenzene wherein each alkyl group is a straight chain of 1-4 carbon atoms with isobutene in the presence of a hydrogen fluoride catalyst at a temperature of from about −50° C. to about 100° C. and a pressure of from about 0 psig to about 150 psig to form 1,3-dialkyl-5-tertiary-butylbenzene;

(b) contacting the 1,3-dialkyl-5-tertiary-butylbenzene with nitric acid in the presence of a soluble mercuric salt catalyst at a temperature of from about 0° C. to about 100° C. to form 2-nitro-1,3-dialkyl-5-tertiary-butylbenzene;

(c) contacting the 2-nitro-1,3-dialkyl-5-tertiary-butylbenzene with hydrogen in the presence of a hydrogenation catalyst at a temperature of from about 0° C. to about 200° C. and a pressure of from about 0 psig to about 2000 psig to form 2,6-dialkyl-4-tertiary-butylaniline;

(d) heating the 2,6-dialkyl-4-tertiary-butylaniline at a temperature of from about 50° C. to about 500° C. in the presence of a heterogeneous acidic catalyst to thereby obtain a reaction mixture comprising 2,6-dialkylaniline and isobutene; and (e) separating 2,6-dialkylaniline from the reaction mixture.

2. A process according to claim 1, wherein the isobutene formed in (d) is separated from the reaction mixture and recycled back to (a).

3. A process according to claim 1, wherein the nitration reaction of (b) is carried out in the presence of an acetic acid solvent.

4. A process according to claim 1, wherein the hydrogenation catalyst is Raney nickel or palladium.

5. A process according to claim 1, wherein each alkyl group independently is methyl or ethyl.

6. A process according to claim 1, wherein the 1,3-dialkylbenzene is meta-xylene.

7. A process according to claim 1, wherein the reaction with isobutene is carried out at a temperature of from about −10° C. to about 50° C. and a pressure of from about 0 psig to about 30 psig.

8. A process according to claim 1, wherein the nitration reaction is carried out at a temperature of from about 50° C. to about 80° C.

9. A process according to claim 1, wherein the hydrogenation reaction is carried out at a temperature of from about 80° C. to about 140° C. and a pressure of from about 50 psig to about 500 psig.

10. A process according to claim 1, wherein step (d) is carried out at a temperature of about 250° C. to about 350° C.

11. A process according to claim 1, wherein about 0.9 to 1.1 moles of isobutene are employed per mole of 1,3-dialkylbenzene.

12. A process according to claim 1, wherein about 1 to 1.2 moles of nitric acid are employed per mole of 1,3-dialkyl-5-tertiary-butylbenzene.

13. A process according to claim 1, wherein about 3 to 3.3 moles of hydrogen are employed per mole of 2-nitro-1,3-dialkyl-5-tertiary-butylbenzene.

14. A process according to claim 1, wherein the mercuric salt is mercuric acetate.

15. A process according to claim 1, wherein the heterogeneous acidic catalyst is silica-alumina.

16. A process for the preparation of 2,6-dimethylaniline which comprises:

(a) contacting meta-xylene with isobutene in the presence of a hydrogen fluoride catalyst at a temperature of from about −50° C. to about 100° C. and a pressure of from about 0 psig to about 150 psig to form 1,3-dimethyl-5-tertiary-butylbenzene;

(b) contacting the 1,3-dimethyl-5-tertiary-butylbenzene with nitric acid in the presence of a mercuric acetate catalyst at a temperature of from about 0° C. to about 100° C. to form 2-nitro-1,3-dimethyl-5-tertiary-butylbenzene;

(c) contacting the 2-nitro-1,3-dimethyl-5-tertiarybutylbenzene with hydrogen in the presence of a hydrogenation catalyst at a temperature of from about 0° C. to about 200° C. and a pressure of from about 0 psig to about 2000 psig to form 2,6-dimethyl-4-tertiary-butylaniline;

(d) heating the 2,6-dimethyl-4-tertiary-butylaniline at a temperature of from about 50° C. to about 500° C. in the presence of a silica-alumina catalyst to thereby obtain a reaction mixture comprising 2,6-dimethylaniline and isobutene; and (e) separating 2,6-dimethylaniline from the reaction mixture.

17. A process according to claim 16, wherein the isobutene formed in (d) is separated from the reaction mixture and recycled back to (a).

* * * * *